(12) United States Patent
Lai et al.

(10) Patent No.: US 7,804,986 B2
(45) Date of Patent: Sep. 28, 2010

(54) SYSTEM AND METHOD FOR DETECTING INTERVERTEBRAL DISC ALIGNMENT USING VERTEBRAE SEGMENTATION

(75) Inventors: Shang-Hong Lai, Saratoga, CA (US); Benjamin Odry, West New York, NJ (US); Li Zhang, Skillman, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1035 days.

(21) Appl. No.: 11/468,852

(22) Filed: Aug. 31, 2006

(65) Prior Publication Data

US 2007/0173744 A1     Jul. 26, 2007

Related U.S. Application Data

(60) Provisional application No. 60/716,676, filed on Sep. 13, 2005.

(51) Int. Cl.
*G06K 9/00* (2006.01)

(52) U.S. Cl. .................................................. 382/128

(58) Field of Classification Search ................ 382/128, 382/130, 131, 132, 173, 162, 164, 181, 190, 382/195, 199, 205, 206, 224; 600/300; 128/920
See application file for complete search history.

(56) References Cited

U.S. PATENT DOCUMENTS

| | | | | |
|---|---|---|---|---|
| 5,627,907 A * | 5/1997 | Gur et al. | ..................... | 382/132 |
| 6,167,167 A * | 12/2000 | Matsugu et al. | ............. | 382/283 |
| 6,396,939 B1 * | 5/2002 | Hu et al. | ..................... | 382/128 |
| 2002/0191827 A1 * | 12/2002 | Armato et al. | ............. | 382/131 |
| 2003/0086599 A1 * | 5/2003 | Armato et al. | ............. | 382/131 |
| 2003/0099397 A1 * | 5/2003 | Matsugu et al. | ............. | 382/173 |
| 2004/0252870 A1 * | 12/2004 | Reeves et al. | ............... | 382/128 |
| 2005/0152588 A1 * | 7/2005 | Yoshida et al. | ............. | 382/128 |
| 2006/0110017 A1 * | 5/2006 | Tsai et al. | .................... | 382/128 |
| 2006/0251302 A1 * | 11/2006 | Abufadel et al. | ............ | 382/128 |
| 2007/0047790 A1 * | 3/2007 | Dewaele | ..................... | 382/128 |

* cited by examiner

*Primary Examiner*—Andrew W Johns
*Assistant Examiner*—Tahmina Ansari (57) ABSTRACT

A computer-implemented method for intervertebral disc alignment includes providing a spine image and a click point on the spine image, applying an adaptive thresholding technique to segment vertebrae regions at the click point from the spine image, and filtering segmented vertebrae regions with a morphological operation. The method further includes estimating a multi-scale orientation field from filtered segmented vertebrae regions, extracting an intervertebral disc region by applying region growing for each scale, integrating the multi-scale orientation field in a locally segmented intervertebral disc region based on the intervertebral disc region, estimating a disc centerline from the filtered segmented vertebrae regions, and fusing an integrated multi-scale orientation field with the disc centerline based on associated confidence measures to provide an intervertebral disc alignment.

16 Claims, 6 Drawing Sheets

SYSTEM AND METHOD FOR DETECTING INTERVERTEBRAL DISC ALIGNMENT USING VERTEBRAE SEGMENTATION

This application claims the benefit of Provisional Application No. 60/716,676 filed on Sep. 13, 2005 in the United States Patent and Trademark Office, the contents of which are herein incorporated by reference in its entirety.

BACKGROUND OF THE INVENTION

1. Field of the Invention

The present disclosure relates to image processing, and more particularly to a system and method for detecting intervertebral disc alignment.

2. Description of Related Art

Magnetic resonance (MR) spine imaging has been widely used for non-invasive detection of different abnormalities and diseases in the spinal column, vertebrae, and inter-vertebral disks. Determining intervertebral disc alignment can be useful in diagnosing and treating these abnormalities and diseases in the spinal column, vertebrae, and inter-vertebral disks.

Therefore, a need exists for a system and method for detecting intervertebral disc alignment.

SUMMARY OF THE INVENTION

According to an embodiment of the present disclosure, a computer-implemented method for intervertebral disc alignment includes providing a spine image and a click point on the spine image, applying an adaptive thresholding technique to segment vertebrae regions at the click point from the spine image, and filtering segmented vertebrae regions with a morphological operation. The method further includes estimating a multi-scale orientation field from filtered segmented vertebrae regions, extracting an intervertebral disc region by applying region growing for each scale, integrating the multi-scale orientation field in a locally segmented intervertebral disc region based on the intervertebral disc region, estimating a disc centerline from the filtered segmented vertebrae regions, and fusing an integrated multi-scale orientation field with the disc centerline based on associated confidence measures to provide an intervertebral disc alignment.

The confidence measures of the orientation field are determined by a gradient magnitude.

Fusing further comprises an iterative re-weighted least square estimation applied to provide the intervertebral disc alignment. The iterative re-weighted least square estimation is applied for the estimated multi-scale orientation filed at different scales, these multi-scale orientation field estimates are integrated based on weighted averaging with a weight for each scale.

The disc center is determined for each scale to be an average of all points in a segmented vertebrae region and a weighted average of these disc centers for each scale with the same weights is determined for the multi scale orientation field.

A centerline between an adjacent vertebrae region is determined by minimizing a distance along a normal direction to the disc orientation.

According to an embodiment of the present disclosure, a program storage device is provided, readable by machine, tangibly embodying a program of instructions executable by the machine to perform method steps for intervertebral disc alignment. The method steps includes providing a spine image and a click point on the spine image, applying an adaptive thresholding technique to segment vertebrae regions at the click point from the spine image, and filtering segmented vertebrae regions with a morphological operation. The method further includes estimating a multi-scale orientation field from filtered segmented vertebrae regions, extracting an intervertebral disc region by applying region growing for each scale, integrating the multi-scale orientation field in a locally segmented intervertebral disc region based on the intervertebral disc region, estimating a disc centerline from the filtered segmented vertebrae regions, and fusing an integrated multi-scale orientation field with the disc centerline based on associated confidence measures to provide an intervertebral disc alignment.

According to an embodiment of the present disclosure, a program storage device is provided readable by machine, tangibly embodying a program of instructions executable by the machine to perform method steps for intervertebral disc alignment, the method steps including providing an integrated multi-scale orientation field in a segmented intervertebral disc region between adjacent vertebrae, providing an estimated a disc centerline between the adjacent vertebrae, and fusing an integrated multi-scale orientation field with the disc centerline based on associated confidence measures to provide an intervertebral disc alignment.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

According to an embodiment of the present disclosure, an intervertebral disc alignment method uses vertebrae segmentation information from spinal MRI. The method applies an adaptive thresholding technique to segment the vertebrae regions and employs a robust intervertebral centerline estimation algorithm to determine the intervertebral disc alignment result. The focus is on finding the orientation and location of the intervertebral disc around the region of a user-provided click point, which is assumed to be located inside the intervertebral disc region.

Figure 1:
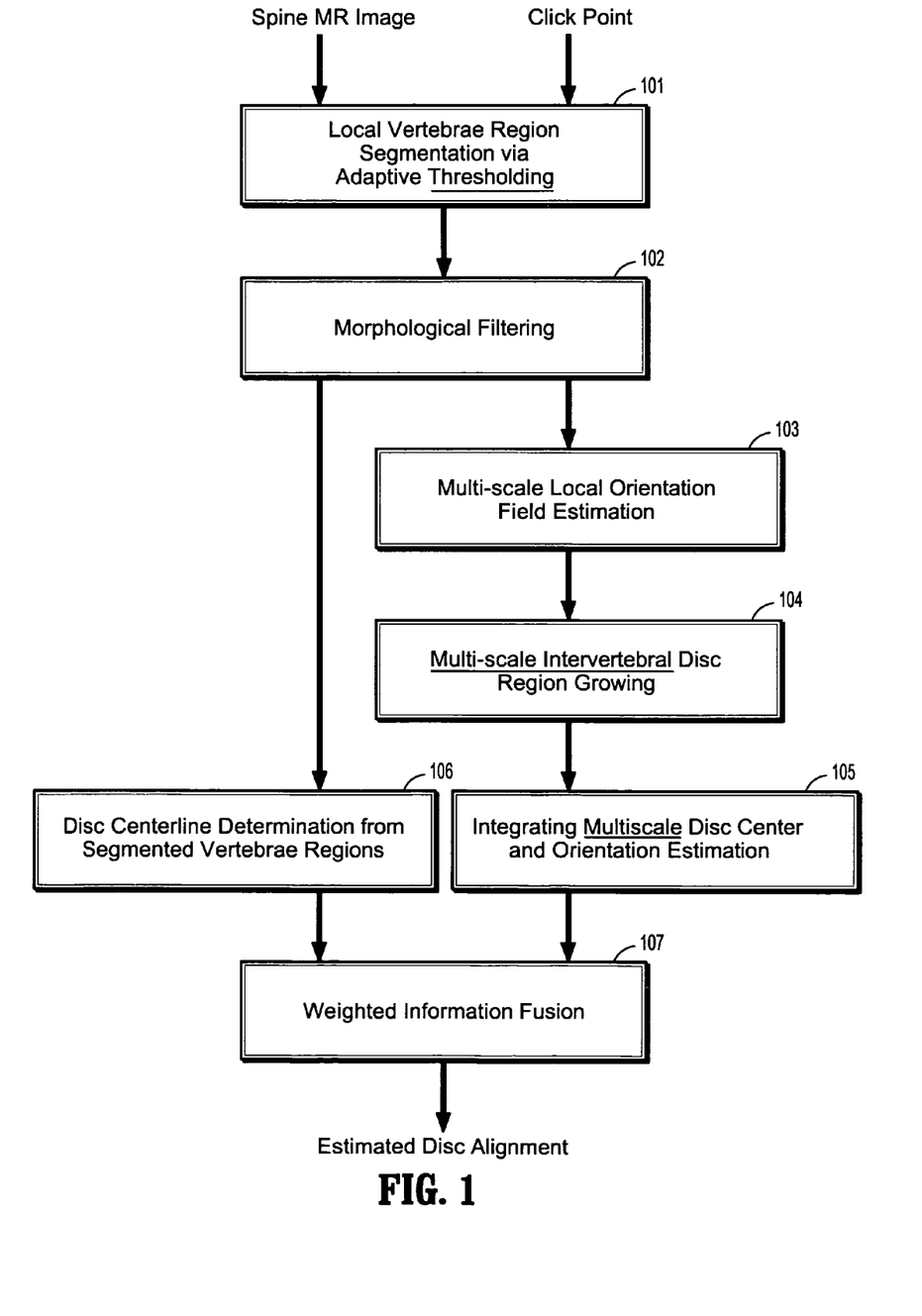
FIG. 1 is a flow chart of a method for estimating disc alignment according to an embodiment of the present disclosure.

Referring to FIG. 1, an intervertebral disc alignment method includes applying an adaptive thresholding technique to segment the vertebrae regions close to the user click point from the spine MR image (101). The segmented vertebrae regions are filtered with morphological operation for hole filling and noise removal (102). Subsequently, the multi-scale orientation field is determined (103), followed by extracting the intervertebral disc region by applying the region growing method for each scale (104). The disc center and orientation are estimated from two complementary approaches including estimation from vertebrae segmentation information (106) and estimation from the computed orientation field in the locally segmented intervertebral disc region (105). These two estimates are integrated based on their associated confidence measures to provide the final intervertebral disc alignment (107).

Referring now to the adaptive thresholding for vertebral segmentation (101), the method needs to detect the upper and lower vertebras around the user-provided click-point. For consistency purpose, this first step of segmentation with threshold is essential. Indeed, the vertebras' regions are needed to accurately locate the inter-vertebral disk for the orientation computation. The vertebrae segmentation allows to accurately position the slice package for further scanning issues. The slice package usually is represented by a box parallel to the disk orientation, user-defined, including one or several vertebras and indicates the region to be scanned.

Referring to the histogram interpretation, the histogram of the whole MR slice is determined instead of computing a local histogram around the click point. This allows to obtaining the same threshold wherever a user clicks on the intervertebral disk and avoid inconsistency issue due histogram differences. The shape of the histogram obtained is specific to the MR spine; typically the background is dark, the vertebras with a middle intensity and other parts, such as the spinal canal, which are brighter.

Figure 2A:
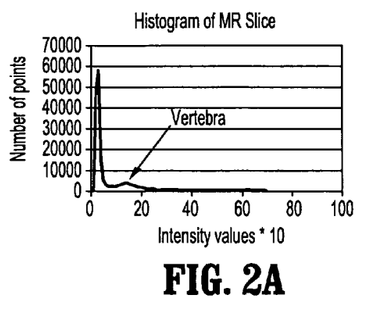
FIGS. 2A-B are a histogram of a slice of a spine and a cropped region of an original slice, according to an embodiment of the present disclosure.
Figure 2B:
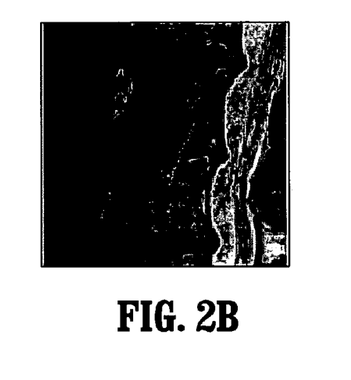

FIG. 2A shows a histogram of MR slice of the spine and FIG. 2B is a cropped region of original slice.

The peak location that corresponds to the vertebra as well as its width are determined using a gradient on the histogram curve $$\nabla H_v(x) = \left(\frac{\partial H_s(x)}{\partial x}\right).$$

The shape of the peak is assimilated to a Gaussian curve and then get the thresholds using the Gaussian sigma σ around the peak.

Referring now to vertebrae selection; once the image information is restricted to the vertebras' range of intensity, a region of interest is set around the user-provided click-point. The size of this region of interest can be adjusted upon the type of vertebrae that is targeted (e.g., cervical, thoracic, lumbar). A binary region that contains at least both upper vertebra and lower vertebra is obtained.

Regions are labeled using a blob-coloring algorithm. Regions that are not vertebrae-like are eliminated. Elimination process is based on the shape of the region (elongated) as well as the location within the region of interest.

Morphology operators such as the opening operator are individually applied to smooth out the shape of the remaining labeled regions and to get rid of unnecessary parts. The process is reiterated in case no vertebrae have been detected, signifying the presence of noise around the vertebras. Final selection process is done based on the location of the remaining regions in regard to the click-point. The two closest regions that are above and below the click point are selected.

Referring to FIG. 3: FIG. 3A shows an exemplary binary image after double threshold application, FIG. 3B is a labeled image, and FIG. 3C is a segmentation after smoothing.

Figure 3A:
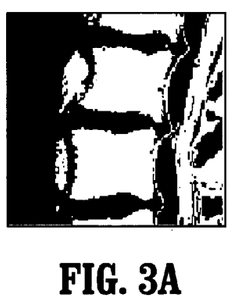
FIGS. 3A-C are a progression of images of a spine according to an embodiment of the present disclosure.
Figure 3B:
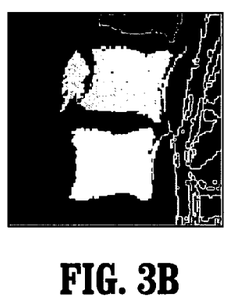
Figure 3C:
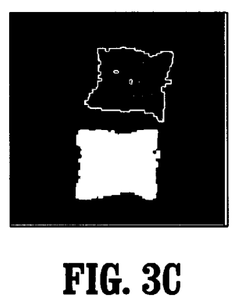
Figure 3D:
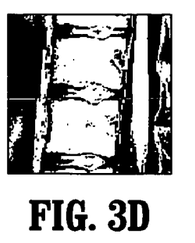
FIGS. 3D-G are a progression of images of a spine according to an embodiment of the present disclosure.
Figure 3E:
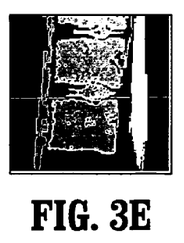
Figure 3F:
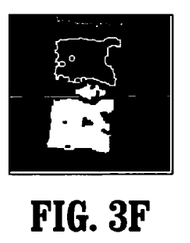
Figure 3G:
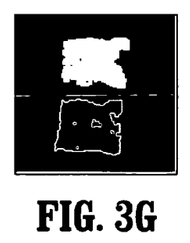

Further, FIG. 3D shows another exemplary binary image after double thresholding, FIG. 3E shows a labeled image, vertebras are not separated, FIG. 3F shows labeled vertebras after separation with opening operator, and FIG. 3G shows a segmentation result.

The sizes and borders of each vertebra are stored for ulterior computation of a slice package dimensions and position between the vertebrae.

Referring to morphological filtering (102), the segmentation of the two neighboring vertebrae regions around the user click point by using the adaptive thresholding technique is usually noisy. Thus, some morphological operations are applied to filter the segmented vertebrae regions. The morphological operations contain an erosion operator followed by a dilation operator. FIG. 4 shows two examples of vertebrae region segmentation results.

Figure 4A:
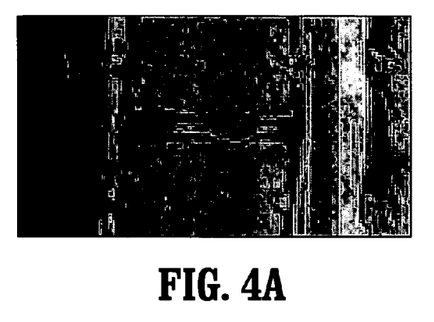
FIGS. 4A and 4C are examples of original spinal images and FIGS. 4B and 4D are examples of vertebrae segmentations according to an embodiment of the present disclosure.
Figure 4B:
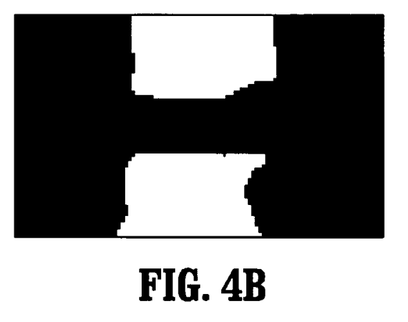
Figure 4C:
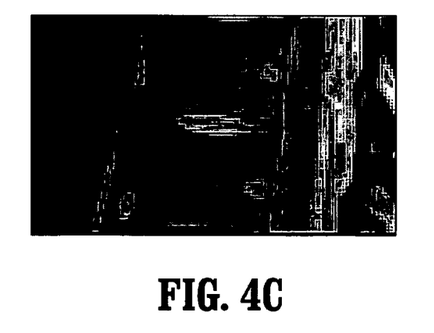
Figure 4D:
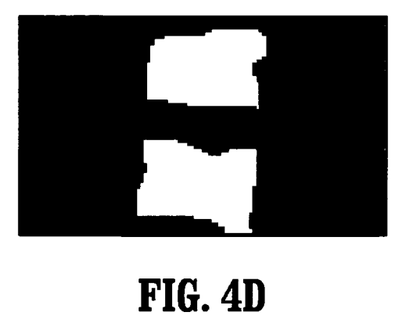

More particularly, FIGS. 4A-D show examples of vertebrae segmentation after the adaptive thresholding and morphological filtering. FIGS. 4A and 4C are the original spinal MR images around the click points, and FIGS. 4B and 4D are the vertebrae segmentation results.

Referring now to the multiscale image orientation estimation (103) and disc region segmentation (104), the image orientation field estimation (103) is based on the following procedure:

1. Compute the 2D convolution of the original image I(x,y) with a 2D Gaussian function $G_o(x,y)$ to be the Gaussian filtered image Is(x,y).

2. Compute the image gradient $$\nabla I_s(x, y) = \left(\frac{\partial I_s(x, y)}{\partial x}, \frac{\partial I_s(x, y)}{\partial y}\right).$$

3. For each pixel, the image gradient covariance matrix C is determined, given by $$C(x, y) = \begin{bmatrix} \sum_{(u,v) \in W(x,y)} \left(\frac{\partial I_s(u, v)}{\partial x}\right)^2 & \sum_{(u,v) \in W(x,y)} \left(\frac{\partial I_s(u, v)}{\partial x} \cdot \frac{\partial I_s(u, v)}{\partial y}\right) \\ \sum_{(u,v) \in W(x,y)} \left(\frac{\partial I_s(u, v)}{\partial x} \cdot \frac{\partial I_s(u, v)}{\partial y}\right) & \sum_{(u,v) \in W(x,y)} \left(\frac{\partial I_s(u, v)}{\partial y}\right)^2 \end{bmatrix}$$

where W(x,y) is a local window center at the pixel (x,y).

4. Compute the eigenvalues, $\lambda_1$ and $\lambda_2$ with $\lambda_1 \geq \lambda_2$, and the associated eigenvectors, v1 and v2, of the matrix C(x,y) for each pixel (x,y).

5. Set the unit orientation vector at each pixel to be the corresponding eigenvector v2, and compute the associated isotropy measure as follows:

$$ISO(x, y) = 1 - \frac{\lambda_2(x, y)}{\lambda_1(x, y) + c},$$

where c is a small positive constant to avoid dividing by zero.

Note that for the determination of the 2D convolution of the original image, the spatial constant σ in the 2D Gaussian function can be chosen appropriately for different scales. Thus, the spatial constant σ can be set it to different values to achieve multi-scale orientation field computation. This may be performed by employing three different values for the spatial constant σ to cover different variations of the image scale in spinal MRI.

Once the multi-scale image orientation field is computed (103), a constrained region growing procedure (104) is applied to segment the intervertebral disc region. The constrained disc region growing is to restrict the disc region to grow into the previously segmented vertebral regions. Let the two segmented vertebral regions be denoted by V1 and V2. This region growing procedure (104) is given as follows:

1. Set the mid-point of the two segmented vertebral regions to be the seed of the disc region D.
2. Find all the neighbors $q_i \notin D \cup V_1 \cup V_2$, for i=1, ..., n, of each pixel p in the disc point set D. For each qi, check the following two criteria:

$$|\theta(q_i) - \hat{\theta}_D| \leq \delta_\theta$$

$$|I_s(q_i) - \bar{I}_D| \leq \delta_I$$

where $\theta(q_i)$ and $\hat{\theta}_D$ denote the orientation angle at the candidate pixel location $q_i$ and the current disc region D, respectively, $\bar{I}_D$ is the average value of the smoothed intensity values inside the disc region, and $\delta_\theta$ and $\delta_I$ are the thresholds for the orientation and intensity consistency checks, respectively. It the two criteria are satisfied, the neighbor candidate point $q_i$ is included into the disc set D.

3. Update the average disc orientation angle $\hat{\theta}_D$ and intensity value $\bar{I}_D$ based on a weighted combination of all pixels in the disc set D with the weight being the corresponding isotropy measure.
4. If the size of the disc set D increases in step 2 and is less a threshold, go back to step 2 and repeat the process. Otherwise, stop the iterative process.

Similarly, the above region growing process is applied for each different scale in the Gaussian smoothing parameter, thus leading to multi-scale orientation estimation and disc region segmentation (104).

Figure 5A:
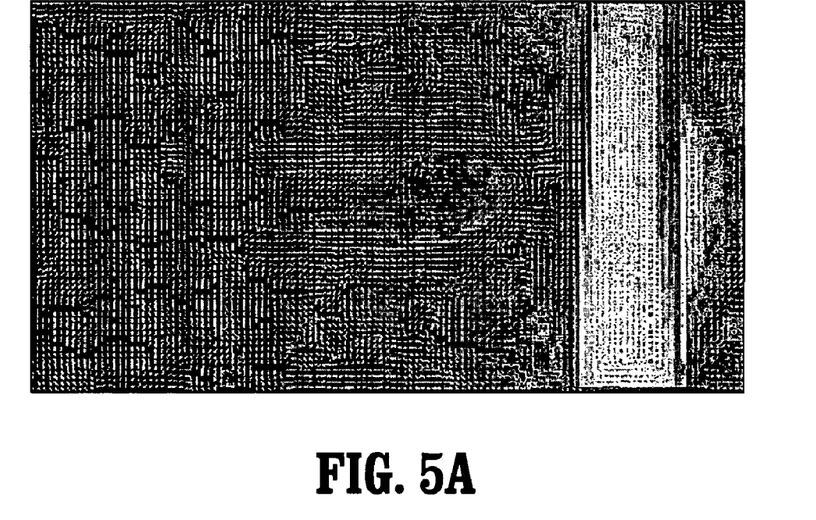
FIGS. 5A-B are a computed orientation field overlaid onto a spinal image and a segmented local intervertebral disc region, respectively, according to an embodiment of the present disclosure.
Figure 5B:
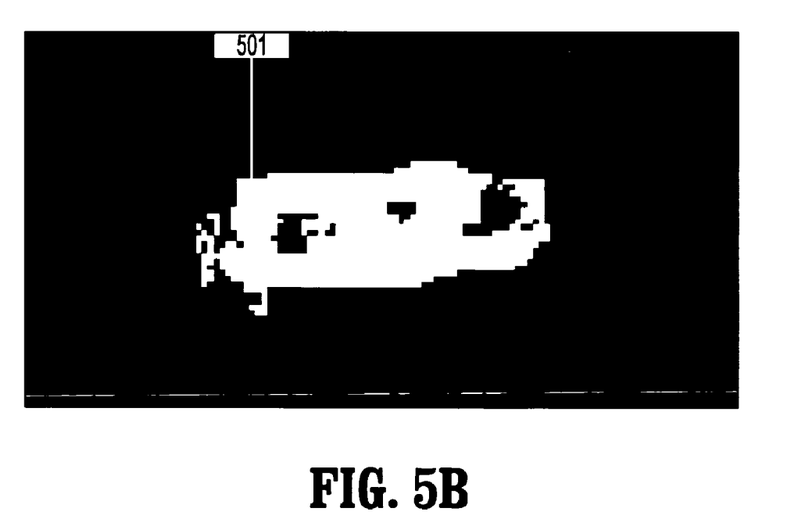

In FIGS. 5A-B, an example of orientation field estimation and intervertebral disc segmentation result from a local spinal MR image are shown.

More particularly, FIG. 5A shows an example of the computed orientation field overlaid onto the local spinal MR image and FIG. 5B shows the segmented local intervertebral disc region 501 obtained from the constrained region growing procedure.

Two complimentary approaches for intervertebral disc alignment are employed. One is based on integrating the multiscale orientation estimation and disc region segmentation (105) to provide the disc orientation and center estimation. The other approach is based on finding the centerline between the two segmented vertebrae regions (106). These different centerline estimates are combined based on their associated confidence weighting to provide an estimation disc alignment (107).

For integrating multiscale orientation estimation and disc segmentation, at each scale, the disc orientation estimation is determined via robust M-estimation, which is implemented in an iterative re-weighted least squares framework. For the re-weighted least square estimation, an initial orientation estimate is determined by using a weighted average of the orientation field inside the segmented disc region, which may be expressed as:

$$\hat{\theta}_0 = \frac{\sum_{(x,y) \in D} |\nabla I_s(x, y)| \hat{\theta}(x, y)}{\sum_{(x,y) \in D} |\nabla I_s(x, y)|}$$

where $\hat{\theta}(x,y)$ is the local orientation estimate at location (x,y) and $|\nabla I_s(x,y)|$ is the magnitude of the corresponding image gradient at the same location. This means the confidence of the orientation estimate is determined by the gradient magnitude. After the initial estimate is computed, the following iterative re-weighted least square estimation is applied to achieve robust estimation of disc orientation.

1. Set k=0, initialize $\hat{\theta}_0$, and compute $$\sigma_0^2 = \frac{1}{|D|} \sum_{(x,y) \in D} \left(\hat{\theta}(x, y) - \hat{\theta}_0\right)^2$$

2. Compute the residues $r(x,y) = \hat{\theta}(x,y) - \hat{\theta}_k$, for all (x,y) in D.
3. Compute the weights $$w(x, y) = \frac{|\nabla I_s(x, y)|}{1 + r^2(x, y)/\sigma_k^2}$$

4. Update the orientation estimate and variance as follows $$\hat{\theta}_{k+1} = \frac{\sum_{(x,y) \in D} w(x, y)\hat{\theta}(x, y)}{\sum_{(x,y) \in D} w(x, y)}$$

$$\sigma_{k+1}^2 = \frac{\sum_{(x,y) \in D} w(x, y)\left(\hat{\theta}(x, y) - \hat{\theta}_{k+1}\right)^2}{\sum_{(x,y) \in D} w(x, y)}$$

5. Set k=k+1.
6. If not converged, return to 2.

After the above iterative re-weighted least square estimation is applied for the disc orientation estimation at different scales, these multiscale orientation estimates are integrated based on weighted averaging with the weight for each scale given by $$w_i = \frac{\sum_{(x,y) \in D} ISO_i(x, y)}{\frac{\hat{\sigma}_i^2}{\sigma_{ref}^2} + 1}$$

Note that the index i in the above equation denotes the scale index, $\hat{\sigma}_i^2$ is the converged variance value in the iterative re-weighted least square procedure, and $\hat{\sigma}_{ref}^2$ is a constant selected empirically for appropriately normalizing the variance values across different scales.

For the disc center estimate, the disc center is determined for each scale to be the average of all points in the segmented vertebrae region D and the weighted average of these disc centers for different scales with the same weights is determined for multiscale orientation integration.

Figure 6:
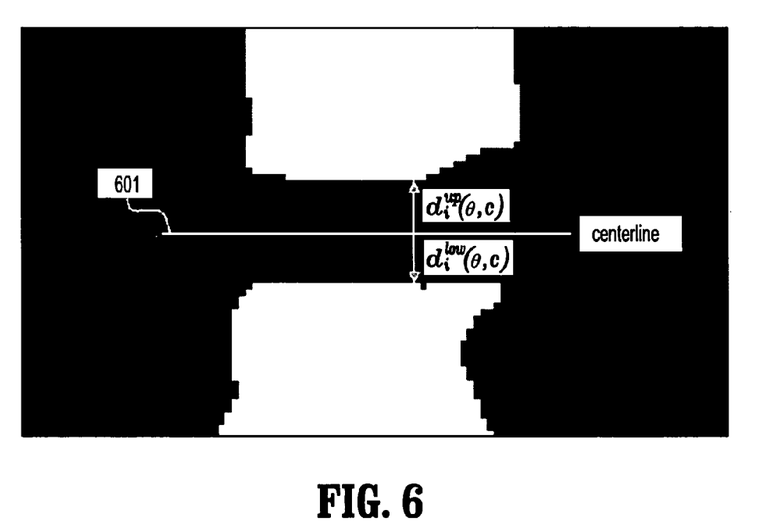
FIG. 6 illustrates a centerline between neighboring vertebrae regions according to an embodiment of the present disclosure.

The other approach for finding the intervertebral disc alignment is to find the centerline between the two segmented vertebrae regions. The centerline between the two vertebrae regions are determined by minimizing the distance function:

$$d(\theta, c) = \frac{1}{n(\theta, c)} \sum_{i=1}^{n(\theta,c)} |d_i^{up}(\theta, c) - d_i^{low}(\theta, c)|$$

where $\theta$ is the centerline orientation angle, c is the center of the disc region, $d_i^{up}(\theta,c)$ and $d_i^{low}(\theta,c)$ are the distances from the i-th point on the centerline to the nearest points in the upper and lower vertebrae regions along the normal direction as depicted in FIG. 6, and $n(\theta,c)$ is the total number of points on the centerline with both $d_i^{up}(\theta,c)$ and $d_i^{low}(\theta,c)$ within a reasonable finite range. To minimize the above distance function, a search is performed on the centerline parameters within a small range since the vertebrae segmentation results can provide a good initial guess of the centerline.

FIG. 6 shows the centerline 601 between two neighboring vertebrae regions with the upper and lower distances $d_i^{up}(\theta,c)$ and $d_i^{low}(\theta,c)$ from the i-th point on the centerline to the upper and lower vertebrae regions shown, respectively.

Two complementary approaches for centerline estimation have been described. These two different centerline estimates are combined based on their corresponding confidence measures. For the multiscale orientation field estimation approach, its confidence weight based on the coherence of the orientation estimation across and within scales is determined. A variance of the orientation estimation for each scale is determined as follows:

$$\overline{\sigma}_i^2 = \hat{\sigma}_i^2 + (\hat{\theta}_i - \overline{\theta})^2,$$

where $\hat{\theta}_i$ and $\hat{\sigma}_i^2$ are the converged orientation angle and variance value in the iterative re-weighted least square procedure, $\overline{\theta}$ is the multiscale integrated orientation estimate, and $\overline{\sigma}_i^2$ the corrected variance of orientation estimation at the i-th scale. The corrected variances for all the scales are combined based on the corresponding weight $w_i$. Thus, the integrated orientation variance $\overline{\sigma}^2$ can be given by:

$$\overline{\sigma}^2 = \sum_i w_i \hat{\sigma}_i^2.$$

The magnitude of the integrated orientation variance indicates the confidence measure of the orientation estimation. The corresponding weighting for the multiscale orientation estimation approach is given by $$w_{orientation} = e^{-\sigma^2/\sigma_{ref}^2}$$

For the centerline estimation from the segmented vertebrae regions, a confidence weight is assigned based on the corresponding average distance function given above as follows:

$$w_{distance} = e^{-d_{min}/d_{ref}}$$

where dmin is the searched minimal distance of the centerline and dref is a constant for appropriate normalization. In the described implementation, the constant dref is empirically set to 5.

Figure 7A:
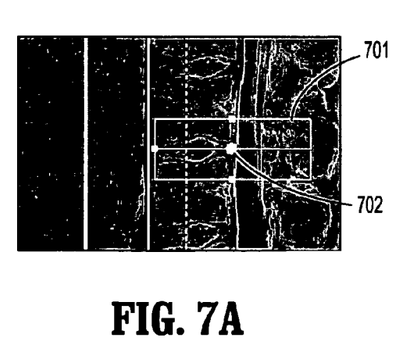
FIGS. 7A-B are examples of a intervertebral disc alignment according to an embodiment of the present disclosure.
Figure 7B:
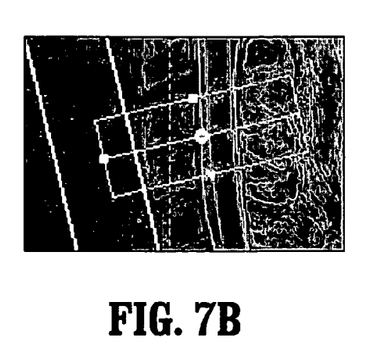

Examples of intervertebral disc alignment by using the proposed algorithm are illustrated in FIG. 7 showing the disc alignment on a local region of the slice from the saggital view of a 3D volumetric spinal MR image. Note that the disc alignment takes a user provided click point inside the disc region so that the region of interest in the MR image can be determined.

More particularly, FIG. 7 shows two examples of the final intervertebral disc alignment by using a method according to an embodiment of the present disclosure. The box 701 is the slice package, automatically defined but user adjustable. The center of the slice package (disc 702) is placed between the two vertebras and at the limit with the spinal canal. Vertebras segmentation is used to place the slice package as well as the saturation band (white lines).

The same process is applied to a coronal view and allows for a 3D orientation of the intervertebral disc to be produced.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 8:
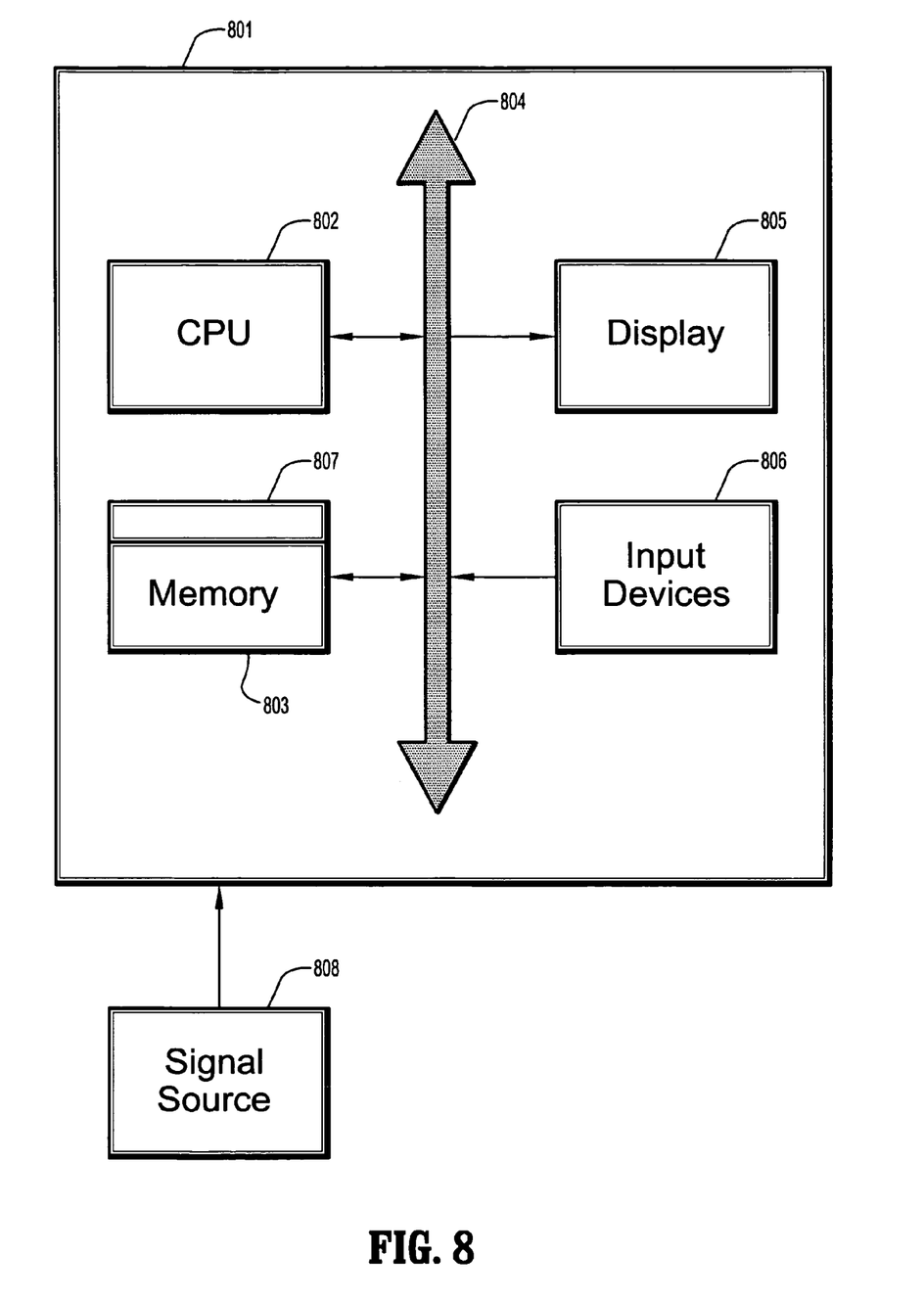
FIG. 8 is a diagram of a system according to an embodiment of the present disclosure.

Referring to FIG. 8, according to an embodiment of the present disclosure, a computer system 801 for intervertebral disc alignment can comprise, inter alia, a central processing unit (CPU) 802, a memory 803 and an input/output (I/O) interface 804. The computer system 801 is generally coupled through the I/O interface 804 to a display 805 and various input devices 806 such as a mouse and keyboard. The support circuits can include circuits such as cache, power supplies, clock circuits, and a communications bus. The memory 803 can include random access memory (RAM), read only memory (ROM), disk drive, tape drive, etc., or a combination thereof. The present invention can be implemented as a routine 807 that is stored in memory 803 and executed by the CPU 802 to process the signal from the signal source 803. As such, the computer system 801 is a general-purpose computer system that becomes a specific purpose computer system when executing the routine 807 of the present invention.

The computer platform 801 also includes an operating system and microinstruction code. The various processes and functions described herein may either be part of the microinstruction code or part of the application program (or a combination thereof), which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present disclosure provided herein, one of ordinary skill in the related art will be able to contemplate these and similar implementations or configurations.

Having described embodiments for a system and method for intervertebral disc alignment, it is noted that modifications and variations can be made by persons skilled in the art in light of the above teachings. It is therefore to be understood that changes may be made in embodiments of the present disclosure that are within the scope and spirit thereof.

What is claimed is:

1. A computer-implemented method for intervertebral disc alignment comprising:
   providing a spine image and a click point on the spine image;
   applying an adaptive thresholding technique to segment vertebrae regions at the click point from the spine image;
   filtering segmented vertebrae regions with a morphological operation;
   estimating a multi-scale orientation field from filtered segmented vertebrae regions;
   extracting an intervertebral disc region by applying region growing for each scale;
   integrating the multi-scale orientation field in a locally segmented intervertebral disc region based on the intervertebral disc region;
   estimating a disc centerline traversing a spinal axis from the filtered segmented vertebrae regions; and
   fusing an integrated multi-scale orientation field with the disc centerline based on associated confidence measures to provide an intervertebral disc alignment.

2. The compute implemented method of claim 1, wherein the confidence measures of the orientation field are determined by a gradient magnitude.

3. The computer-implemented method of claim 1, wherein fusing further comprises an iterative re-weighted least square estimation applied to provide the intervertebral disc alignment.

4. The computer-implemented method of claim 3, wherein the iterative re-weighted least square estimation is applied for an estimated multi-scale orientation field at different scales, the multi-scale orientation field estimates are integrated based on weighted averaging with a weight for each scale.

5. The computer-implemented method of claim 1, wherein the disc center is determined for each scale to be an average of all points in a segmented vertebrae region and a weighted average of these disc centers for each scale with the same weights is determined for the multi-scale orientation field.

6. The computer-implemented method of claim 1, wherein a estimating the disc centerline further comprises determining the disc centerline by minimizing distances from points on the disc centerline to respective nearest points on adjacent ones of the filtered segmented vertebrae regions along a normal direction to the disc orientation.

7. A non-transitory computer-readable medium embodying instructions executed by a processor to perform method steps for intervertebral disc alignment, the method steps comprising:
   providing a spine image and a click point on the spine image;
   applying an adaptive thresholding technique to segment vertebrae regions at the click point from the spine image;
   filtering segmented vertebrae regions with a morphological operation;
   estimating a multi-scale orientation field from filtered segmented vertebrae regions;
   extracting an intervertebral disc region by applying region growing for each scale;
   integrating the multi-scale orientation field in a locally segmented intervertebral disc region based on the intervertebral disc region;
   estimating a disc centerline traversing a spinal axis from the filtered segmented vertebrae regions; and
   fusing an integrated multi-scale orientation field with the disc centerline based on associated confidence measures to provide an intervertebral disc alignment.

8. The method of claim 7, wherein the confidence measures of the orientation field are determined by a gradient magnitude.

9. The method of claim 7, wherein fusing further comprises an iterative re-weighted least square estimation applied to provide the intervertebral disc alignment.

10. The method of claim 9, wherein the iterative re-weighted least square estimation is applied for an estimated multi-scale orientation field at different scales, the multi-scale orientation field estimates are integrated based on weighted averaging with a weight for each scale.

11. The method of claim 7, wherein the disc center is determined for each scale to be an average of all points in a segmented vertebrae region and a weighted average of these disc centers for each scale with the same weights is determined for the multi-scale orientation field.

12. The method of claim 7, wherein estimating the disc centerline further comprises determining the disc centerline by minimizing distances from points on the disc centerline to respective nearest points on adjacent ones of the filtered segmented vertebrae regions along a normal direction to the disc orientation.

13. A non-transitory computer-readable medium embodying instructions executed by a processor to perform method steps for intervertebral disc alignment, the method steps comprising:
   providing an integrated multi-scale orientation field in a segmented intervertebral disc region between adjacent vertebrae;
   providing an estimated disc centerline traversing a spinal axis between the adjacent vertebrae; and
   fusing an integrated multi-scale orientation field with the disc centerline based on associated confidence measures to provide an intervertebral disc alignment.

14. The method of claim 13, wherein the confidence measures of the orientation field are determined by a gradient magnitude.

15. The method of claim 13, wherein fusing further comprises an iterative re-weighted least square estimation applied to provide the intervertebral disc alignment.

16. The method of claim 15, wherein the iterative re-weighted least square estimation is applied for an estimated multi-scale orientation field at different scales, the multi-scale orientation field estimates are integrated based on weighted averaging with a weight for each scale.

* * * * *